United States Patent
Batista et al.

(10) Patent No.: US 11,882,879 B2
(45) Date of Patent: Jan. 30, 2024

(54) AEROSOL-GENERATING DEVICE COMPRISING MULTIPLE SENSORS

(71) Applicant: Philip Morris Products S.A., Neuchatel (CH)

(72) Inventors: Rui Nuno Batista, Neuchatel (CH); Chiara Fasciani, Neuchatel (CH)

(73) Assignee: Philip Morris Products S.A., Neuchatel (CH)

(*) Notice: Subject to any disclaimer, the term of this patent is extended or adjusted under 35 U.S.C. 154(b) by 808 days.

(21) Appl. No.: 16/961,586

(22) PCT Filed: Jan. 11, 2019

(86) PCT No.: PCT/EP2019/050645
§ 371 (c)(1),
(2) Date: Jul. 10, 2020

(87) PCT Pub. No.: WO2019/138043
PCT Pub. Date: Jul. 18, 2019

(65) Prior Publication Data
US 2020/0367570 A1    Nov. 26, 2020

(30) Foreign Application Priority Data
Jan. 12, 2018   (EP) ..................... 18151510

(51) Int. Cl.
*A24F 40/46* (2020.01)
*A24F 40/51* (2020.01)
(Continued)

(52) U.S. Cl.
CPC .............. *A24F 40/46* (2020.01); *A24F 40/42* (2020.01); *A24F 40/51* (2020.01); *A24F 40/57* (2020.01); *A24F 40/10* (2020.01); *A24F 40/48* (2020.01)

(58) Field of Classification Search
CPC .......... A24F 40/46; A24F 40/51; A24F 40/57; A24F 40/40
See application file for complete search history.

(56) References Cited

U.S. PATENT DOCUMENTS

| 8,967,155 B2 | 3/2015 | Bundren et al. |
| 9,138,017 B2 | 9/2015 | Garrett et al. |
| (Continued) | | |

FOREIGN PATENT DOCUMENTS

| CN | 204146307 U | 2/2015 |
| CN | 105774478 A | 7/2016 |
| (Continued) | | |

OTHER PUBLICATIONS

Japanese Office Action dated Mar. 1, 2023 in Japanese Patent Application No. 2020-536841 (with English translation), 5 pages.
(Continued)

*Primary Examiner* — Hae Moon Hyeon
(74) *Attorney, Agent, or Firm* — Oblon, McClelland, Maier & Neustadt, L.L.P.

(57) ABSTRACT

An aerosol-generating device is provided, including: an air inlet; an air outlet; an air flow passage extending in a first direction between the air inlet and the air outlet; a heating element in the air flow passage configured to heat an aerosol-forming substrate; a first temperature sensor configured to measure a first temperature at a first position along the air flow passage; a second temperature sensor spaced apart in the first direction from the first sensor configured to measure a second temperature at a second position along the air flow passage; and a controller configured to control an operating parameter of the aerosol-generating device based on the measured first temperature and the measured second temperature.

17 Claims, 5 Drawing Sheets

(51) Int. Cl.
*A24F 40/57* (2020.01)
*A24F 40/42* (2020.01)
*A24F 40/48* (2020.01)
*A24F 40/10* (2020.01)

(56) References Cited

U.S. PATENT DOCUMENTS

| 10,090,693 | B2* | 10/2018 | Alarcon | H02J 7/0042 |
|---|---|---|---|---|
| 2009/0133691 | A1 | 5/2009 | Yamada et al. | |
| 2010/0051815 | A1 | 3/2010 | Lee | |
| 2011/0100114 | A1 | 5/2011 | de Corral | |
| 2016/0235122 | A1 | 8/2016 | Krietzman | |
| 2016/0235123 | A1 | 8/2016 | Krietzman | |
| 2016/0235124 | A1 | 8/2016 | Krietzman | |
| 2017/0150755 | A1* | 6/2017 | Batista | A24F 40/42 |
| 2017/0196273 | A1 | 7/2017 | Qiu | |
| 2017/0238610 | A1 | 8/2017 | Reevell | |
| 2017/0245553 | A1 | 8/2017 | Reevell | |
| 2019/0029322 | A1 | 1/2019 | Krietzman | |
| 2022/0225685 | A1* | 7/2022 | Blackmon | A24F 40/53 |

FOREIGN PATENT DOCUMENTS

| CN | 106488714 A | 3/2017 | |
|---|---|---|---|
| CN | 106535680 A | 3/2017 | |
| CN | 107373763 A | 11/2017 | |
| EP | 2 047 880 A1 | 4/2009 | |
| RU | 2 517 100 C2 | 5/2014 | |
| WO | WO 2008/015918 A1 | 2/2008 | |
| WO | WO 2009/091703 A1 | 7/2009 | |
| WO | WO 2016/184783 A1 | 11/2015 | |
| WO | WO 2017/140898 A1 | 8/2017 | |
| WO | WO 2018/054793 A1 | 3/2018 | |
| WO | WO 2019/138055 A1 | 7/2019 | |
| WO | WO-2019138043 A1 * | 7/2019 | A24F 40/40 |

OTHER PUBLICATIONS

Extended European Search Report dated Jul. 18, 2018 in Patent Application No. 181515107, 8 pages.
Juan C. Scaiano, et al., "Tuning Plasmon Transitions and their Applications in Organic Photochemistry" Pure Appl. Chem., vol. 83, No. 4, 2011, pp. 913-930.
Chiara Fasciani, et al., "High-Temperature Organic Reactions at Room Temperature Using Plasmon Excitation: Decomposition of Dicumyl Peroxide" Organic Letters, vol. 13, No. 2, 2011 pp. 204-207.
C. J. Bueno Alejo, et al. "Reduction of Resazurin to Resorufin Catalyzed by Gold Nanoparticles: Dramatic Reaction Acceleration by Laser or LED Plasmon Excitation" Catalysis Science & Technology, vol. 1, 2011, pp. 1506-1511.
Kevin G. Stamplecoskie, et al., "Dual-Stage Lithography from a Light-Driven, Plasmon-Assisted Process: A Hierarchical Approach to Subwavelength Features" Langumir, vol. 28, pp. 10957-10961.
Katherine L. McGilvray, et al., "Photochemical Strategies for the Seed-Mediated Growth of Gold and Gold-Silver Nanoparticles" Langmuir, vol. 28, 2012, pp. 16148-16155.
Chiara Fasciani, et al., "Aspartame-Stabilized Gold-Silver Bimetallic Biocompatible Nanostructures with Plasmonic Photothermal Properties, Antibacterial Activity and Long-Term Stability" Just Accepted Manuscript DOI: 10.1021/ja510435u, Journal of the American Chemical Society, Dec. 3, 2014, 7 pages.
Eduardo A. Coronado, et al., "Optical Properties of Metallic Nanoparticles: Manipulating Light, Heat and Forces at the Nanoscale" Nanoscale, vol. 3, 2011, 4042-4059.
Hyunbong Choi, et al., "*Know Thy Nano Neighbor*. Plasmonic versus Electron Charging Effects of Metal Nanoparticles in Dye-Sensitized Solar Cells" ACSNANO, 2012, vol. 6, No. 5, pp. 4418-4427.
Cláudia Gomes Silva, et al., "Influence of Excitation Wavelength (UV or Visible Light) on the Photocatalytic Activity of Titania Containing Gold Nanoparticles forthe Generation of Hydrogen or Oxygen from Water" Journal of the American Chemical Society, vol. 133, 2011, pp. 595-602.
Prashant V. Kamat, et al., "Electrochemical Modulation of Fluorophore Emission on a Nanostructured Gold Film" Angew. Chem. Int. Ed., vol. 41, 2002, pp. 2764-2767.
Binil Itty Ipe, et al. "Photoinduced Charge Separation in a Fluorophore-Gold Nanoassembly" J. Phys. Chem. B, vol. 106, No. 1, 2002, pp. 18-21.
Theo Baum, et al., "Electrochemical Charge Injection into Immobilized Nanosized Gold Particle Ensembles: Potential Modulated Transmission and Reflectance Spectroscopy" Langmuir, vol. 15, No. 3, 1999, pp. 866-871.
Shaowei Chen, et al., "Electrochemical Quantized Capacitance Charging of Surface Ensembles of Gold Nanoparticles" J. Phys. Chem. B, vol. 103, No. 45, 1999, pp. 9996-10000.
Shaowei Chen, et al., "Gold Nanoelectrodes of Varied Size: Transition to Molecule-Like Charging" Science, vol. 280, Jun. 26, 1998, pp. 2098-2101 cover page.
Saïd Barazzouk, et al., "Photoinduced Electron Transfer between Chlorophyll a and Gold Nanoparticles" J. Phys. Chem. B, vol. 109, No. 2, 2005, pages 716-723.
Natalia L. Pacioni, et al., "Surface Plasmons Control the Dynamics of Excited Triplet States in the Presence of Gold Nanoparticles" J. Am.Chem. Soc., vol. 132, No. 18, 2010, pp. 6298-6299.
Juan C. Scaiano, et al., "Can Surface Plasmon Fields Provide a New Way to Photosensitize Organic Photoreactions? From Designer Nanoparticles to Custom Applications" The Journal of Physical Chemistry Letters, vol. 4, 2013, pp. 1177-1187.
Paul Mulvaney, "Surface Plasmon Spectroscopy of Nanosized Metal Particles" Langmuir, vol. 12, No. 3, 1996, pp. 788-800.
Silvia Underwood, et al., "Effect of the Solution Refractive Index on the Color of Gold Colloids" Langmuir, vol. 10, No. 10, 1994, pp. 3427-3430.
Kevin, G. Stamplecoskie, et al., "Light Emitting Diode Irradiation Can Control the Morphology and Optical Properties of Silver Nanoparticles" J. Am. Chem. Soc., vol. 132, No. 6, 2010, pp. 1825-1827.
Juan C. Scaiano, et al., "Photochemical Routes to Silver and Gold Nanopartides" Pure Appl. Chem. vol. 81, No. 4, 2009, pp. 635-647.
M. Luisa Marin, et al., "Photochemical Strategies for the Synthesis of Gold Nanoparticles from Au(III) and Au(I) Using Photoinduced Free Radical Generation" J. Am. Chem. Soc. vol. 130, No. 49, 2008, pp. 16572-16584.
Emilio I. Alarcon, et al., "The Biocompatibility and Antibacterial Properties of Collagen-Stabilized, Photochemically Prepared Silver Nanoparticles" Biomaterials, vol. 33, 2012, pp. 4947-4956.
Steffen Jockusch, et al., "Photochemistry and Photophysics of α-Hydroxy Ketones" Macromolecules, vol. 34, No. 6, 2001, pp. 1619-1626.
Katherine L. McGilvray, et al., "Facile Photochemical Synthesis of Unprotected Aqueous Gold Nanoparticles" J. Am. Chem. Soc., vol. 128, 2006, pp. 15980-15981.
A. Callegari, et al., "Photochemically Grown Silver Nanoparticles with Wavelength-Controlled Size and Shape" Nano Letters, vol. 3, No. 11, 2003, pp. 1565-1568.
Jin, Rongchao, et al., "Controlling Anisotropic Nanoparticle Growth through Plasmon Excitation" Nature, vol. 425, Oct. 2, 2003, pp. 487-490.
Rongchao Jin, "Photoinduced Conversion of Silver Nanospheres to Nanoprisms" Science, vol. 294, Nov. 30, 2001, pp. 1901-1903.
A. C. Sant'Ana, et al., "Size-dependent SERS Enhancement of Colloidal Silver Nanoplates: the Case of 2-Amino-5-Nitropyridine" Journal of Raman Spectroscopy, vol. 40, 2009, pp. 183-190.
Masanori Sakamoto, et al., "Light as a Construction Tool of Metal Nanoparticles: Synthesis and Mechanism" Journal of Photochemistry Photobiology C: Photochemistry Reviews, vol. 10, 2009, pp. 33-56.
G. V. Krylova, et al., "Photochemical Preparation of Nanoparticles of Ag in Aqueous-Alcoholic Solutions and on the Surface of Mesoporous Silica" Theoretical and Experimental Chemistry, vol. 41, No. 2, 2005, pp. 105-110.

(56) References Cited

OTHER PUBLICATIONS

H. H. Huang, et al., "Photochemical Formation of Silver Nanoparticles in Poly(N-vinylpyrrolidone)" Langmuir, vol. 12, 1996, pp. 909-912.
Xiao Shuang Shen, et al., "Anisotropic Growth of One-Dimensional Silver Rod-Needle and Plate-Belt Heteronanostructures Induced by Twins and hcp Phase" J. Am. Chem. Soc., vol. 131, 2009, pp. 10812-10813.
Joseph A. Webb, et al., "Emerging Advances in Nanomedicine with Engineered Gold Nanostructures" Nanoscale, vol. 6, 2014, pp. 2502-2530.
Guillaume Baffou, et al., "Thermo-Plasmonics: Using Metallic Nanostructures as Nana-Sources of Heat" Laser Photonics Rev. vol. 7, No. 2, 2013, pp. 171-187.
Guillaume Baffou, et al., "Femtosecond-Pulsed Optical Heating of Gold Nanoparticles" Phys. Rev. B, vol. 84, 2011, pp. 1-13.
G. Mie, "Beitrage zur Optik Truber Medien, Speziell Kolloidaler Metallosungen" Annalen der Physik, vol. 25, No. 3, 1908, pp. 377-445.
Richard P. Feynman, "There's Plenty of Room at the Bottom" Journal of Microelectromechanical System, vol. 1, No. 1, Mar. 1992, pp. 60-66.
Michael Faraday, "Experimental Relations of Gold (and other Metals) to Light" Phil. Trans. R. Soc. 1857, 147, pp. 145-181.
Philippe Sciau, "Nanoparticles in Ancient Materials: the Metallic Lustre Decorations of Medieval Ceramics" The Delivery of Nanoparticles, Cap.25, 2012, pp. 525-540 with Cover pages.
G. Schmid, "Clusters and Colloids: From Theory to Application" Advanced Materials, vol. 7, No. 1, 1995, 1 page.
"Mass Flow Controller Measurement Technology: A Review" Alicat Scientific, http://www.alicat.com/alicat-blog/mass-flow-controller-measurement-technology-a-review/, 2017, 3 pages.
"Sensing Temperature On-Chip" Moortec, http://www.moortec.com/page/31/embedded-on-chip-temperature-sensing-ip, 2017, 1 page.
"How to Use the on-Chip Temperature Sensor XMC1000" Infineon, https://www.infineon.com/dgdl/Infineon-ApplicationNote_How_To_Use_On-Chip_Temperature_Sensor_XMC1000-AN-v01_03-EN.pdf?fileId=5546d462525dbac401531c6aadc94791, 2016, pp. 1-16.
Decision to Grant dated Oct. 3, 2022 in Russian Patent Application No. 2020125676 (with English translation), 19 pages.
Search Report dated Oct. 3, 2022 in Russian Patent Application No. 2020125676 (with English translation), 19 pages.
Cortie et al., "Plasmonic heating of gold nanoparticles and its exploitation," Institute for Nanoscale Technology, University of Technology Sydney, PO Box 123, Broadway NSW 2007, Australia, Proc. of SPIE vol. 5649, XP055093379, pp. 565-573.
International Search Report and Written Opinion dated Mar. 29, 2019 in PCT/EP2019/050645 filed on Jan. 11, 2019.
Chinese Office Action and Search Report dated Sep. 14, 2023 issued in Chinese Patent Application No. 201980006650.8 filed Jan. 11, 2019, with English Translation, total 17 pages.

* cited by examiner

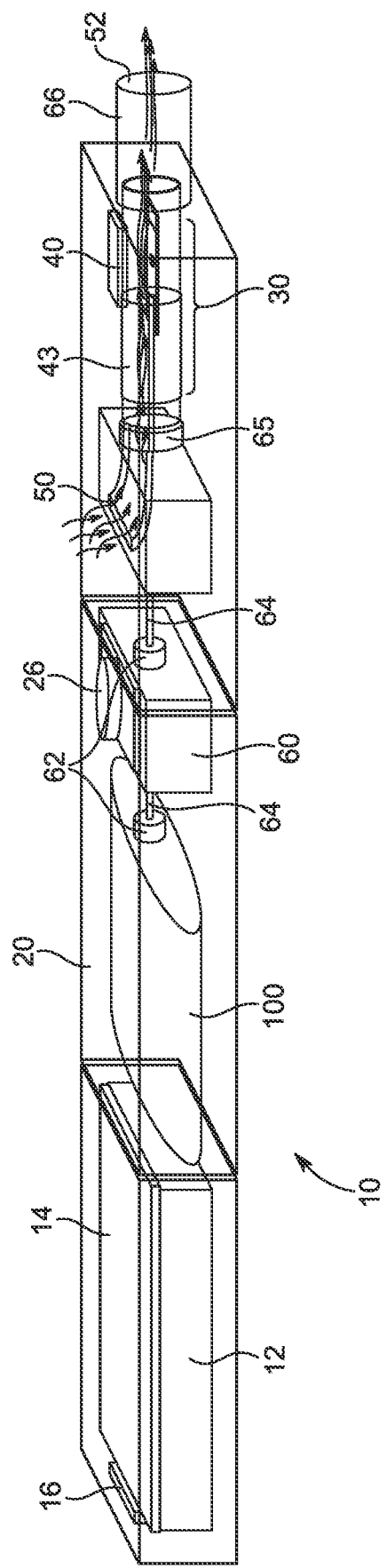

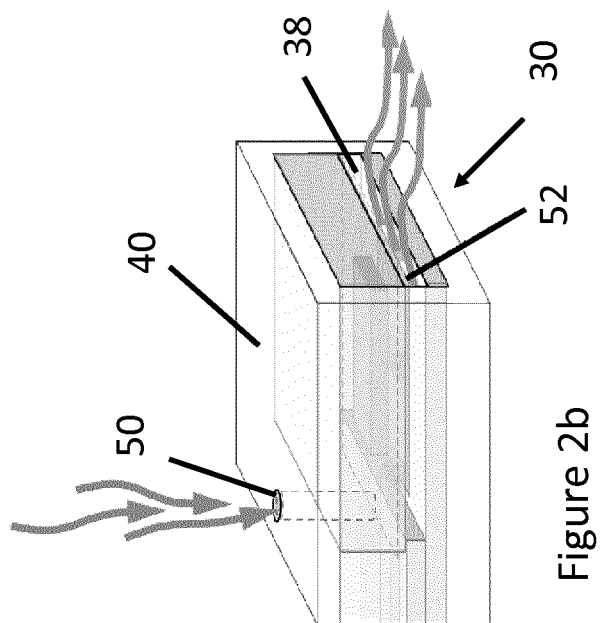
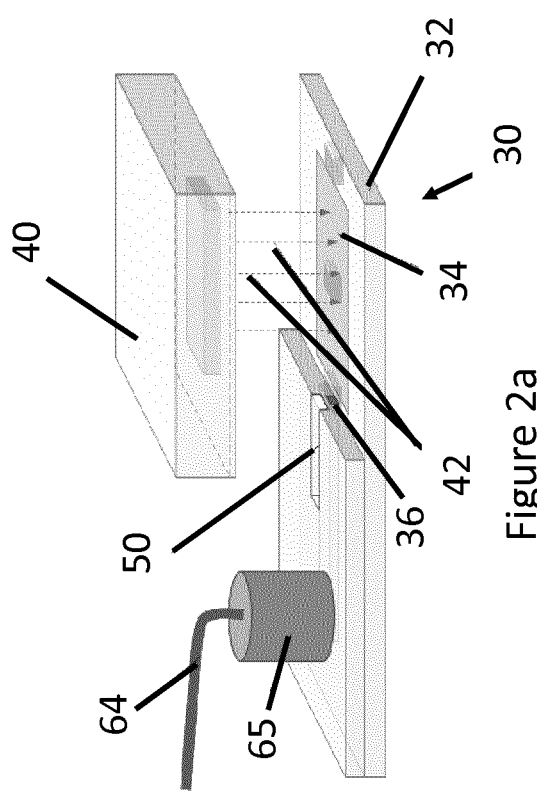
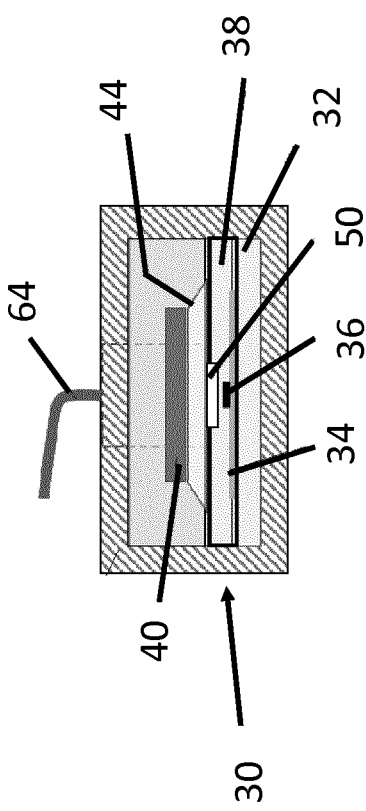
Figure 2b
Figure 2a
Figure 2c

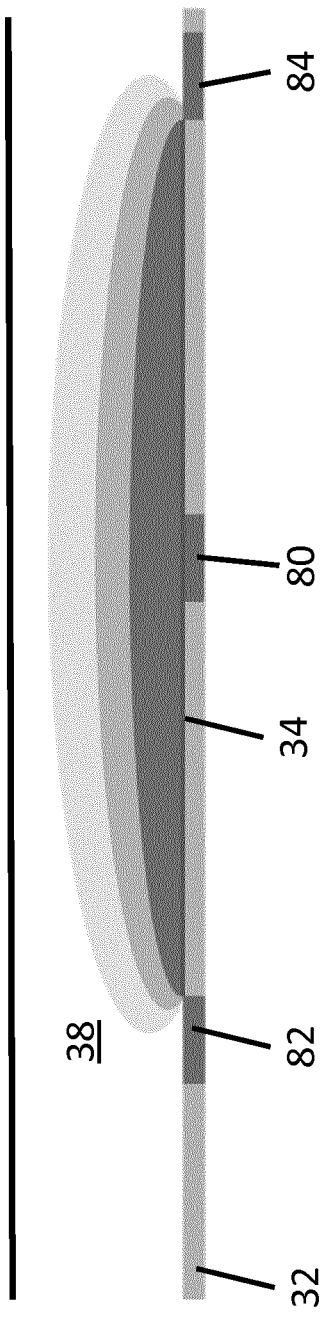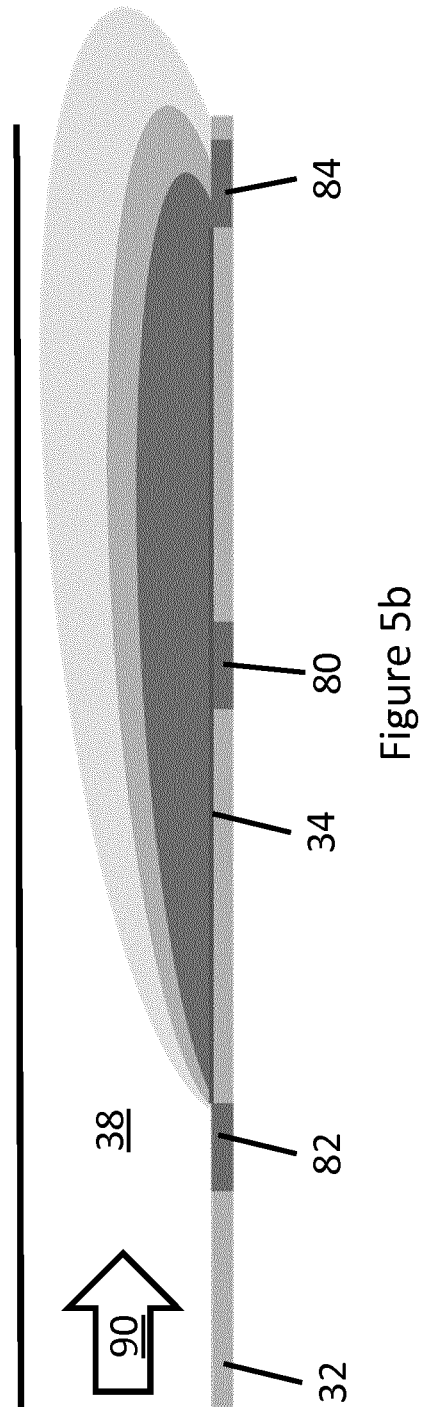

AEROSOL-GENERATING DEVICE COMPRISING MULTIPLE SENSORS

CROSS-REFERENCE TO RELATED APPLICATIONS

This application is a U.S. national stage application of PCT/EP2019/050645, filed on Jan. 11, 2019, which is based upon and claims the benefit of priority under 35 U.S.C. § 119 from European patent application no. 18151510.7, filed Jan. 12, 2018, the entire contents of each of which are incorporated herein by reference.

TECHNICAL FIELD

The present specification relates to an aerosol-generating device for heating an aerosol-forming substrate to generate an aerosol. Particularly, but not exclusively, the invention relates to an aerosol-generating device comprising multiple temperature sensors for controlling an operational parameter of the aerosol-generating device.

DESCRIPTION OF THE RELATED ART

In a number of handheld aerosol-generating devices, a resistive heating element may be used for heating an aerosol-forming substrate to generate an aerosol. The resistive heating element may be controlled by a controller. The controller may be configured to control the operation of the resistive heating element based on a heater temperature, which may be determined by measuring the electrical resistance across the resistive heating element. This may significantly reduce the chance the resistive heating element becoming damaged, for example due to overheating, because the power supplied to the heating element may be restricted when the measured heater temperature exceeds a given threshold value. If the resistive heating element is used to heat a supply of liquid aerosol-forming substrate, and the supply of liquid aerosol-forming substrate becomes depleted, the controller may detect a significant rise in a temperature of the resistive heating element. In response, the controller may prevent the resistive heating element from generating any further heat, by terminating a supply of power to the resistive heating element.

However, such temperature measurements may not be able to detect localised temperature fluctuations at the resistive heating element. This is because the electrical resistance is measured across the entire heater circuit, and thus is representative of the overall temperature of the entire resistive heating element. Moreover, such temperature measurements are not indicative of the temperature at locations in the device other than the heating element. For example, it is difficult to accurately derive an aerosol temperature based on electrical resistance of the resistive heating element alone.

Moreover, the temperature measurement at the resistive heating element is based on measuring the electrical resistance when passing a current through the resistive heating element. Thus the temperature measurement ceases once the resistive heating element is not in operation. That may be problematic or inconvenient. For example, if the controller has terminated power from being supplied to the resistive heating element due to the temperature of the resistive heating element exceeding a threshold value, then, the controller will not be able to continue to determine the temperature of the resistive heating element. This means that the controller will not be able to determine whether the temperature of the resistive heating element has decreased to below the threshold value, without again supplying power to the resistive heating element. This will cause the temperature of the resistive heating element to increase again. Obviously, temperature measurements of this type only function with a resistive heating element. Thus this technique cannot be used with other types of non-resistive heater based aerosol-generating device.

It would be desirable to provide an aerosol-generating device comprising a heating arrangement that mitigates or overcomes at least some of these disadvantages with known devices. It would be desirable to provide an aerosol-generating device, which may utilise more advanced sensor arrangements, and which may implement an improved control mechanism.

SUMMARY

According to a first aspect of the present invention there is provided an aerosol-generating device comprising: an air inlet; an air outlet; an air flow passage extending in a first direction between the air inlet and the air outlet; a heating element in the air flow passage for heating an aerosol-forming substrate; a first temperature sensor for measuring a first temperature at a first position along the air flow passage; a second temperature sensor spaced apart in the first direction from the first sensor, the second temperature sensor for measuring a second temperature at a second position along the air flow passage; and a controller configured to control an operational parameter of the device based on the measured first temperature and the measured second temperature.

According to a second aspect of the present invention there is provided a liquid storage cartridge comprising a connector for connecting the liquid storage cartridge to an aerosol-generating device, wherein the liquid storage cartridge comprises a liquid aerosol-forming substrate and is configured to collapse upon depletion of aerosol-forming substrate. The depletion of aerosol-forming substrate may not cause a negative pressure in the liquid storage cartridge. Thus it may advantageously prevent air ingression into the cartridge. In some embodiments, the connector is a Luer fitting.

According to a third aspect of the present invention there is provided an aerosol-generating system comprising an aerosol-generating device according to the first and second aspects of the invention and an aerosol-generating article comprising an aerosol-forming substrate. The aerosol generating-article may comprise a liquid storage cartridge comprising the aerosol-forming substrate.

According to a fourth aspect of the present invention there is provided a method of controlling an aerosol-generating device, said aerosol-generating device comprising a heating element in an air flow passage extending in a first direction, the method comprising the steps of: measuring a first temperature at a first position along the air flow passage; measuring a second temperature at a second position along the air flow passage and wherein the second position is spaced apart in the first direction from the first position; and controlling an operational parameter of the device, based on the measured first temperature and the measured second temperature.

According to a fifth aspect of the present invention, there is provided an aerosol-generating device comprising: an air inlet; an air outlet; an air flow passage extending in a first direction between the air inlet and the air outlet; a heating element in the air flow passage for heating an aerosol-forming substrate; a first temperature sensor for measuring a first temperature at a first position along the air flow passage; and a controller configured to control an operational parameter of the device based on at least the measured first temperature.

Features described in relation to one aspect may equally be applied to other aspects of the invention.

BRIEF DESCRIPTION OF THE DRAWINGS

Embodiments of the invention are further described, by way of example only, with reference to the accompanying drawings, in which:

FIG. 1 is a perspective view of an aerosol-generating system according to an embodiment of the present invention:

FIG. 2a is an exploded perspective view of the heater assembly of FIG. 1;

FIG. 2b is a perspective view of the heater assembly of FIG. 1;

FIG. 2c is a sectional view of the heater assembly of FIGS. 2a and 2b;

FIG. 5a is a schematic illustration of heat dissipation at the heating element of FIG. 4, in a first condition, in which there is substantially no air flow across the heating element; and FIG. 5b is a schematic illustration of heat dissipation at the heating element of FIG. 4, in a second condition, in which an air supply is drawn into the aerosol-generating device, across the heating element.

DETAILED DESCRIPTION

Figure 3:
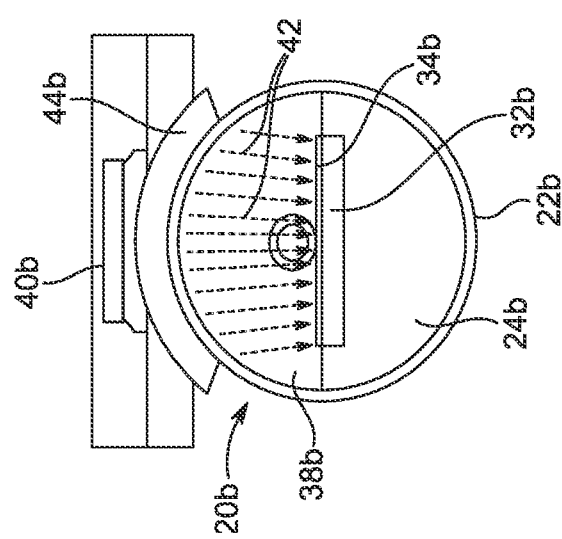
FIG. 3 is a sectional view of the heater assembly according to an embodiment of the present invention.

In some embodiments, the operational parameter may comprise a plurality of operational parameters.

The first temperature sensor and the second temperature sensor may be different types of temperature sensors. The first temperature sensor and the second temperature sensor may be the same type of temperature sensors.

As used herein, the term "temperature sensor" may refer to any suitable sensing means for sensing one or more signals indicative of a temperature. For example, where the heating element comprises a resistive heating element, the resistive heating element and a controller for measuring the electrical resistance across the resistive heating element function as the temperature sensor.

As used herein, the term "measured temperature" may refer to a direct temperature measurement or to an indirect temperature measurement. An indirect temperature measurement may comprise a temperature determined by the controller based on one or more signals indicative of a temperature.

The first position and the second position may be located anywhere along the air flow passage for measuring localised temperatures. Said first temperature may comprise a temperature indicative of any one or combination of: ambient air at the first position, air flowing through the air flow passage at the first position, a generated aerosol in the air flow passage at the first position, the heating element at the first position and an aerosol-forming substrate supplied to the heating element at the first position. Said second temperature may comprise a temperature indicative of any one or combination of: ambient air at the second position, air flowing through the air flow passage at the second position, a generated aerosol in the air flow passage at the second position, the heating element at the second position and an aerosol-forming substrate supplied to the heating element at the second position. The measured temperatures may advantageously permit the controller to control one or more operational parameters of the device based on the localised temperatures as measured at specific known positions along the air flow passage. The measured temperatures may advantageously permit the controller to determine a temperature gradient of the air flow passage, at least along the first direction. The measured temperatures may advantageously permit the controller to determine localised temperature fluctuations at the heating element.

The location of each of the first and second position may be selected to provide one or more advantageous effect, as described in the embodiments discussed below.

The first position may be spaced apart from the heating element. The second position may be spaced apart from the heating element. This may allow for measurement of the temperature at one or more positions along the airflow passage that are spaced apart from the heating element, such as along the first direction along the air flow passage. Advantageously, this may simplify a design of the device, as the temperature sensors may be provided as separate components from the heating element. This makes the heating element easier to service or replace. This may also be advantageous when there is a desire to determine the temperature of an aerosol after it has been generated at the heating element. This may be advantageous when there is a desire to determine the temperature of an air supply at a position before the air reaches the heating element, such as at a position where the temperature of the air supply is unlikely to be significantly influenced by heat produced by heating element. The first position and the second position may each be spaced at an equal distance apart from the heating element along the air flow passage.

The first position may be immediately adjacent to the heating element, in either an upstream or downstream direction relative to the heating element. The second position may be immediately adjacent to the heating element, in either an upstream or downstream direction relative to the heating element. This may advantageously allow one or both of the first and second temperature sensors to provide an indication of air temperature immediately before the air reaches the heating element. This may advantageously allow one or both of the first and second temperature sensors to provide an indication of an aerosol temperature immediately after the aerosol has been generated at the heating element.

In some embodiments, one of the first position and the second position may be located upstream of the heating element, and the other of the first position and the second position may be positioned downstream of the heating element. In some embodiments, both of the first position and the second position may be positioned upstream of the heating element. In some embodiments, both of the first position and the second position may be positioned downstream of the heating element.

The controller may be configured to control an operational parameter of the device based on the measured first temperature and the measured second temperature. In some embodiments, the controller is configured to control an operational parameter of the device based on a difference between the first temperature and the second temperature. In some embodiments, the controller is configured to control the operational parameter based on a ratio between the first temperature and the second temperature. For example, in some embodiments, the difference between the first temperature and the second temperature may advantageously indicate that one or both of an air supply and a generated aerosol are flowing along at least part of an air flow path, which extends at least between the first position and the second position. More specifically, a sudden increase of one of the first or second temperatures relative to the other, may indicate that such air flow is occurring. This may be particularly relevant if one of the first position and second position is positioned downstream of the heating element, and the other of the first position and second position is positioned upstream of the heating element. This is because a sudden drop in temperature upstream of the heating element may indicate an influx of air supply to the airflow passage. A sudden rise in temperature downstream of the heating element may indicate that an aerosol has been generated at the heating element and is flowing towards the air outlet. Therefore a relative difference or a relative ratio between the first temperature and the second temperature may be indicative of such events.

In some embodiments, one of the first position and the second position may correspond to a position on the heating element and the other of the first position and the second position may be spaced apart from the heating element in a direction along the air flow passage. This may allow for a measured heating element temperature to be compared with a temperature, which is measured upstream or downstream of the heating element. This may advantageously enable the determination of an air flow event. For example, a higher air flow rate may result in a lower temperature being measured downstream to the heating element, than may otherwise be measured if the air flow rate was lower. Thus, the controller may advantageously determine one or more air flow parameters, such as air flow rate, based on the first and second temperatures.

In some embodiments, the controller is configured to determine an air flow event, such as any one or more of: an inhalation, an exhalation or an air flow rate, such as a volumetric air flow rate, based on the measured first temperature and the measured second temperature. This may advantageously allow the controller to control an operational parameter of the device based on a determined air flow event in addition to said first and second temperatures. Indeed, air flow events may impact the measured first and second temperatures. By controlling the operational parameter based on both an air flow event and the first and second temperatures, the device may more accurately control said operational parameter.

In some embodiments, the heating element may comprise a plurality of heating sections. Each of the first position and the second position may be located at a respective heating section of the heating element. Therefore, the measured first temperature may be indicative of the temperature of a first section of the heating element corresponding to the first position. The measured second temperature may be indicative of the temperature of a second section of the heating element corresponding to the second position. This allows the sensors to be used to determine temperatures representative of different sections of the heating element. Advantageously, this enables a temperature gradient across the heating element to be determined. In some embodiments, the controller is arranged to determine a temperature distribution across the heating element and to control the operational parameter based on the determined temperature distribution. In some embodiments, each respective heating section may be independently controllable. Advantageously, this enables any undesired localised temperature fluctuations across the heating element to be corrected for. Indeed, it will be understood that in some embodiments, more than two heating sections may be provided, each respective heating section having a corresponding position from which a corresponding temperature may be measured. A plurality of heating sections with a plurality of positions advantageously enables a more accurate temperature gradient across the heating element to be determined.

In some embodiments, the heating element may comprise a resistive heating element. In such embodiments, one of the first temperature sensor and the second temperature sensor may comprise the resistive heating element and the respective first or second measured temperature may be based on measuring an electrical resistance across the resistive heating element. The first temperature sensor and the second temperature sensor may be different types of temperature sensors. The first temperature sensor and the second temperature sensor may be the same type of temperature sensors.

The heating element may comprise a plasmonic heating element comprising a plurality of metallic nanoparticles arranged to receive light from a light source and generate heat by surface plasmon resonance.

As used herein, the term "surface plasmon resonance" refers to a collective resonant oscillation of free electrons of the metallic nanoparticles and thus polarization of charges at the surface of the metallic nanoparticles. The collective resonant oscillation of the free electrons and thus polarisation of charges is stimulated by light incident on the metallic nanoparticles from a light source. Energy from the oscillating free electrons may be dissipated by several mechanisms, including heat. Therefore, when the metallic nanoparticles are irradiated with a light source, the metallic nanoparticles generate heat by surface plasmon resonance.

As used herein, the term "metallic nanoparticles" refers to metallic particles having a maximum diameter of about 1 micrometre or less. Metallic nanoparticles that generate heat by surface plasmon resonance when excited by incident light may also be known as plasmonic nanoparticles.

Advantageously, a plasmonic heating element arranged to generate heat by surface plasmon resonance may provide more homogenous heating of an aerosol-forming substrate when compared to resistive and inductive heating systems. For example, the free electrons of the metallic nanoparticles are excited to the same extent regardless of an angle of incidence of incident light.

Advantageously, a plasmonic heating element arranged to generate heat by surface plasmon resonance may provide more localised heating when compared to resistive and inductive heating systems. Advantageously, localised heating facilitates heating of discrete portions of an aerosol-forming substrate or a plurality of discrete aerosol-forming substrates. Advantageously, localised heating increases the efficiency of the aerosol-generating device by increasing or maximising the transfer of heat generated by the plasmonic heating element to an aerosol-forming substrate. Advantageously, localised heating may reduce or eliminate undesired heating of other components of the aerosol-generating device.

The plasmonic heating element may be arranged to receive light from an external light source and generate heat by surface plasmon resonance. An external light source may comprise ambient light. Ambient light may comprise solar radiation. Ambient light may comprise at least one artificial light source external to the aerosol-generating device.

The plasmonic heating element may receive ambient light from the ambient light source directly, or it may receive the ambient light via one or more additional light transmitting elements in the device. Ambient light may be received into the aerosol-generating device via one or more windows or openings on the external surface of the aerosol-generating device. The ambient light source may function to supplement the light source of the aerosol-generating device. This may be advantageous when seeking to pre-heat the aerosol-forming substrate to an elevated temperature prior to operating the internal light source of the device. This may also advantageously reduce the amount of power required by the aerosol-generating device. The aerosol-generating device may comprise an ambient light controlling means for controlling the amount of ambient light that light transmitting core may receive from the ambient light source. The ambient light controlling means may comprise an automatic controlling means such as an automatic shutter. The ambient light controlling means may comprise a manual controlling means, such as a releasable cap for covering one or more windows or openings in the device.

The aerosol-generating device may comprise a light source, wherein the plasmonic heating element is arranged to receive light from the light source and generate heat by surface plasmon resonance.

Advantageously, providing the aerosol-generating device with a light source may allow the plasmonic heating element to generate heat without receiving light from an external light source. Advantageously, providing the aerosol-generating device with a light source may provide improved control of the illumination of the plasmonic heating element. Advantageously, controlling the illumination of the plasmonic heating element controls the temperature to which the plasmonic heating element is heated by surface plasmon resonance.

The light source may comprise a light source arranged to emit light in the visible light range of the electromagnetic spectrum. The light source may comprise a light source arranged to emit light beyond the visible light range of the electromagnetic spectrum, such as at least one of an ultraviolet light source and an infrared light source. This may advantageously excite a broader range of nanoparticles, such as nanoparticles of varying sizes or compositions.

Preferably, the light source is configured to emit light comprising at least one wavelength between 380 nanometres and 700 nanometres. Preferably, the light source is configured for a peak emission wavelength of between about 495 nanometres and about 580 nanometres. As used herein, "peak emission wavelength" refers to the wavelength at which a light source exhibits maximum intensity. Advantageously, a peak emission wavelength of between about 495 nanometres and about 580 nanometres may provide maximum heating of the plasmonic heating element by surface plasmon resonance, particularly when the plurality of metallic nanoparticles comprises at least one of gold, silver, platinum, and copper.

The light source of the aerosol-generating device may comprise at least one of a light emitting diode (LED) and a laser.

Advantageously, light emitting diodes and lasers may have a compact size suited to use in an aerosol-generating device. The light sources of the aerosol-generating device may not require a relatively large voltage drop to effect surface plasmon resonance. For example, the light source of the aerosol-generating device may comprise one or more light emitting diodes (LEDs). This may allow for a safer and more cost effective power source to be used to power the device. Moreover, it is not necessary to provide a physical connection between the plasmonic heating element and the light source. Therefore the use of the plasmonic heating element may advantageously reduce the likelihood of damage to the heating element during service and maintenance. Indeed, because a physical connection between the plasmonic heating element and the light source need not be provided, the plasmonic heating element may easily be repaired or replaced. The plasmonic heating element may also mean that the device is less vulnerable to an external environment because the use of the plasmonic heating element may eliminate a need for exposed electrical components.

Using a laser as the light source, may enable the emission of light within a relatively narrow range of wavelengths. The laser may comprise at least one of a solid state laser and a semiconductor laser. The narrow range of wavelengths may be a range of wavelengths matched to the size and composition of the nanoparticles, as will later be described. This may advantageously improve efficiency, most, if not all light outputted by the light source may be absorbed by the metallic nanoparticles to generate heat by surface plasmon resonance. Additionally, such a light source may be relatively robust and simple in construction in comparison to other light sources.

The light emitted by the light source, such as a number of photons emitted per second, may be varied by controlling an amplitude, or a frequency, or a combination of amplitude and frequency of the emitted light. The amount of light emitted by the light source, such as number of photons emitted per second may be varied by emitting light pulses.

The light source may comprise a plurality of light sources. The light sources may be the same type of light source. At least some of the light sources may be different types of light source. The plurality of light sources may comprise any combination of the types of light source described herein.

Advantageously, a plurality of light sources may facilitate customisation of a heating profile generated by the aerosol-generating device during use.

At least one of the light sources may be a primary light source and at least one of the light sources may be a backup light source. The aerosol-generating device may be configured to emit light from one or more backup light sources only when one or more of the primary light sources is inoperative.

At least one of the light sources may be arranged to irradiate only a portion of the plurality of metallic nanoparticles. Each of the plurality of light sources may be arranged to irradiate a different portion of the plurality of metallic nanoparticles.

The aerosol-generating device may be configured so that the plurality of light sources irradiate different portions of the plurality of metallic nanoparticles at the same time. Advantageously, irradiating different portions of the plurality of metallic nanoparticles at the same time may facilitate homogenous heating of the plasmonic heating element. Advantageously, irradiating different portions of the plurality of metallic nanoparticles at the same time may facilitate simultaneous heating of a plurality of discrete aerosol-forming substrates.

The aerosol-generating device may be configured so that the plurality of light sources irradiate different portions of the plurality of metallic nanoparticles at different times. Advantageously, irradiating different portions of the plurality of metallic nanoparticles at different times may facilitate heating of different portions of an aerosol-forming substrate at different times. Advantageously, irradiating different portions of the plurality of metallic nanoparticles at different times may facilitate heating of a plurality of discrete aerosol-forming substrates at different times.

Preferably, the aerosol-generating device comprises an electrical power supply and a controller configured to supply electrical power from the electrical power supply to the light source.

In embodiments in which the aerosol-generating device comprises a plurality of light sources, the electrical power supply may comprise a single source of electrical power arranged to supply electrical power to the plurality of light sources.

In embodiments in which the aerosol-generating device comprises a plurality of light sources, the electrical power supply may comprise a plurality of sources of electrical power arranged to supply electrical power to the plurality of light sources.

In embodiments in which the aerosol-generating device comprises a plurality of light sources, the controller may be configured to selectively supply electrical power to at least some of the plurality of light sources. The controller may be configured to selectively vary a supply of electrical power to at least some of the plurality of light sources.

In embodiments in which the plurality of light sources are configured to irradiate different portions of the plurality of metallic nanoparticles to heat a plurality of discrete aerosol-forming substrates, the controller may selectively supply electrical power to at least some of the plurality of light sources to selectively heat at least some of the plurality of discrete aerosol-forming substrates. The controller may selectively vary a supply of electrical power to at least some of the plurality of light sources to vary a ratio of heating of at least some of the plurality of discrete aerosol-forming substrates.

Advantageously, by varying the relative heating of at least some of a plurality of discrete aerosol-forming substrates, the aerosol-generating device may vary the composition of an aerosol delivered to a user.

Preferably, the aerosol-generating device comprises a user input device. The user input device may comprise at least one of a push-button, a scroll-wheel, a touch-button, a touch-screen, and a microphone. Advantageously, the user input device allows a user to control one or more aspects of the operation of the aerosol-generating device. In embodiments in which the aerosol-generating device comprises a light source, a controller and an electrical power supply, the user input device may allow a user to activate a supply of electrical power to the light source, to deactivate a supply of electrical power to the light source, or both.

In embodiments in which the controller is configured to selectively supply electrical power to at least some of a plurality of light sources, preferably the controller is configured to selectively supply electrical power to at least some of the plurality of light sources in response to a user input received by the user input device.

In embodiments in which the controller is configured to selectively vary a supply of electrical power to at least some of a plurality of light sources, preferably the controller is configured to selectively vary a supply of electrical power to at least some of the plurality of light sources in response to a user input received by the user input device.

The aerosol-generating device may comprise one or more optical elements to facilitate the transmission of light from a light source to the plasmonic heating element. The one or more optical elements may include at least one of an aperture, a window, a lens, a reflector, and an optical fibre.

Advantageously, at least one of an aperture and a window may facilitate the transmission of light from an external light source to the plasmonic heating element. The aerosol-generating device may comprise a housing, wherein at least one of an aperture and a window is positioned on the housing.

Advantageously, at least one of a lens, a reflector and an optical fibre may concentrate or focus light emitted from a light source onto the plasmonic heating element. Advantageously, concentrating or focusing light onto the plasmonic heating element may increase the temperature to which the plasmonic heating element is heated by surface plasmon resonance.

The plurality of metallic nanoparticles may comprises at least one of gold, silver, platinum, copper, palladium, aluminium, chromium, titanium, rhodium, and ruthenium. The plurality of metallic nanoparticles may comprise at least one metal in elemental form. The plurality of metallic nanoparticles may comprise at least one metal in a metallic compound. The metallic compound may comprise at least one metal nitride.

Preferably, the plurality of metallic nanoparticles comprises at least one of gold, silver, platinum, and copper. Advantageously, gold, silver, platinum, and copper nanoparticles may exhibit strong surface plasmon resonance when irradiated with visible light.

The plurality of metallic nanoparticles may comprise a single metal. The plurality of metallic nanoparticles may comprise a mixture of different metals.

The plurality of metallic nanoparticles may comprise a plurality of first nanoparticles comprising a first metal and a plurality of second nanoparticles comprising a second metal.

At least some of the plurality of metallic nanoparticles may each comprise a mixture of two or more metals. At least some of the plurality of metallic nanoparticles may comprise a metal alloy. At least some of the plurality of metallic nanoparticles may each comprise a core-shell configuration, wherein the core comprises a first metal and the shell comprises a second metal.

In embodiments in which the aerosol-generating device comprises a light source, preferably the plurality of metallic nanoparticles comprises a number average maximum diameter that is less than or equal to the peak emission wavelength of the light source.

The plurality of metallic nanoparticles may comprise a number average maximum diameter of less than about 700 nanometres, preferably less than about 600 nanometres, preferably less than about 500 nanometres, preferably less than about 400 nanometres, preferably less than about 300 nanometres, preferably less than about 200 nanometres, preferably less than about 150 nanometres, preferably less than about 100 nanometres.

The plasmonic heating element may be formed from the plurality of metallic nanoparticles.

The plasmonic heating element may comprise a substrate layer and a coating layer positioned on at least a portion of the substrate layer, wherein the coating layer comprises the plurality of metallic nanoparticles. Advantageously, the substrate layer may be formed from a material selected for desired mechanical properties. Advantageously, the coating layer may be formed to optimise the surface plasmon resonance of the plurality of metallic nanoparticles when the coating layer is exposed to light from a light source.

The substrate layer may be formed from any suitable material. The substrate layer may comprise a metal. The substrate layer may comprise a polymeric material. The substrate layer may comprise a ceramic.

The substrate layer may be electrically conductive. The substrate layer may be electrically insulating.

The nanoparticles may be provided on the substrate layer using any suitable process. The metallic nanoparticles may be deposited on the substrate layer using a physical vapour deposition process.

The plasmonic heating element may comprise a plurality of discrete areas of metallic nanoparticles, wherein the plurality of discrete areas are spaced apart from each other. Advantageously, a plurality of discrete areas of metallic nanoparticles may facilitate heating of a plurality of discrete portions of an aerosol-forming substrate. Advantageously, a plurality of discrete areas of metallic nanoparticles may facilitate heating of a plurality of discrete aerosol-forming substrates.

The aerosol-generating device may comprise a light source arranged to irradiate a plurality of the discrete areas of metallic nanoparticles. The aerosol-generating device may comprise a plurality of light sources arranged to irradiate the plurality of discrete areas of metallic nanoparticles. Each of the plurality of light sources may be arranged to irradiate only one of the discrete areas of metallic nanoparticles.

The plasmonic heating element may comprise a first surface arranged to receive light from a light source and generate heat by surface plasmon resonance of the plurality of metallic nanoparticles. The first surface may comprise a plurality of surface features defining a three-dimensional shape. The first surface may comprise at least one of a plurality of protrusions and a plurality of depressions. The first surface may have an undulating shape.

Advantageously, a first surface comprising a plurality of surface features may increase the surface area of the first surface. Advantageously, increasing the surface area of the first surface may increase heating of the plurality of metallic nanoparticles by surface plasmon resonance when light is incident on the first surface.

In embodiments in which the plasmonic heating element comprises a substrate layer and a coating layer, a first surface of the substrate layer may define the plurality of surface features, wherein the coating layer is provided on the first surface of the substrate layer to form the first surface of the plasmonic heating element.

The plasmonic heating element may comprise a second surface arranged to transfer heat to an aerosol-forming substrate during use. The second surface may be on an opposite side of the plasmonic heating element to the first surface. In embodiments in which the plasmonic heating element comprises a substrate layer and a coating layer, preferably the substrate layer comprises a first surface on which the coating layer is provided to form the first surface of the plasmonic heating element, and a second surface forming the second surface of the plasmonic heating element. Preferably, the substrate layer comprises a thermally conductive material to facilitate the transfer of heat from the coating layer to the second surface of the plasmonic heating element.

In embodiments in which the heating element comprises a resistive heating element and a plasmonic heating element, the plurality of metallic nanoparticles may form the resistive heating element.

In embodiments in which the plasmonic heating element comprises a substrate layer and a coating layer, at least one of the substrate layer and the coating layer may form the resistive heating element. The substrate layer may comprise an electrically resistive material. The electrically resistive material may comprise at least one of an electrically resistive metal and an electrically resistive ceramic. The substrate layer may be formed from the electrically resistive material. The substrate layer may comprise a woven material, wherein a plurality of threads of the electrically resistive material form at least part of the woven material.

In embodiments in which the aerosol-generating device comprises an electrical power supply and a controller, preferably the controller is arranged to provide a supply of electrical power from the electrical power supply to the resistive heating element.

The aerosol-generating device may be arranged to generate heat using the resistive heating element in addition to generating heat by surface plasmon resonance of the plurality of metallic nanoparticles. The aerosol-generating device may be arranged to generate heat using the resistive heating element as an alternative to generating heat by surface plasmon resonance of the plurality of metallic nanoparticles.

The aerosol-generating device may be arranged to generate heat using the resistive heating element as a backup to generating heat by surface plasmon resonance of the plurality of metallic nanoparticles. For example, the aerosol-generating device may be arranged to generate heat using the resistive heating element in the event that heating of the plurality of metallic nanoparticles by surface plasmon resonance is insufficient.

The aerosol-generating device may be arranged to generate heat using the resistive heating element at the start of a heating cycle. In other words, the resistive heating element may be used to generate heat to raise the temperature of the heating element to an initial operating temperature. The aerosol-generating device may be arranged to reduce or terminate a supply of electrical power to the resistive heating element when the temperature of the heating element reaches an initial operating temperature.

The operational parameter of the device may affect the operation of one or more components of the device. The operational parameter may comprise one or more process variables that affect the operation of one or more components of the device. Preferably, the one or more components comprise one or more components used by the device to generate an aerosol, such as the heating element or a power supply configured to supply power directly or indirectly to the heating element. For example, in some embodiments, the operational parameter may comprise a temperature of the heating element. The operational parameter may comprise a temperature profile of the heating element, such as output temperature over time. The temperature or the temperature profile may be controlled by the controller controlling power supplied to the heating element from a power supply. The power may be supplied directly to the heating element. The power may be supplied indirectly to the heating element, for example by supplying electrical power to one or more light sources, which are arranged to provide light to a plasmonic heating surface of the heating element. The controller may be configured to control an output temperature of at least a portion of the heating element based on the measured first temperature and the measured second temperature. In the above discussed embodiments where the first and second positions are located at different heating sections along the heating element, the controller may be configured to independently control an operational parameter associated with each of the heating sections, based on the respective first and the second measured temperatures. For example, the controller may be configured to determine a temperature distribution across the plurality of heating sections, and may individually control the power supplied to each of the plurality of heating sections based on the determined temperature distribution. This can allow for more precise control the heat produced by the heating element. Control of the power supplied to the plurality of heating sections may be achieved by controlling the electrical power supplied to one or more of a plurality of light sources, which are arranged to provide light to power each of the respective heating sections of the heating element. For example, if a first light source is arranged to provide light to a first heating section and a second light source is arranged to provide light to a second heating section, the controller may be configured to increase the amount of light emitted by the second light source relative to the amount of light emitted by the first light source, if a measured temperature corresponding the second section of the heating element has been determined to be lower than a measured temperature corresponding the first section of the heating element.

In some embodiments, the controller may be configured to activate or otherwise control the amount of heat dissipated by the heating element upon detection of an air flow. In some embodiments, the controller may be configured to control the operational parameter based on the determined air flow rate. For example, the controller may be configured to control the temperature of the heating element based on a volumetric rate of air flow through the air flow passage.

In some embodiments, the aerosol-generating device may comprise: a liquid storage portion comprising the aerosol-forming substrate; and a pump for pumping the aerosol-forming substrate from the liquid storage portion to the heating element; wherein the operational parameter of the device comprises a flow rate of aerosol-forming substrate from the liquid storage portion to the heating element, wherein the controller is arranged to control the flow rate of aerosol-forming substrate based on the measured first temperature and the measured second temperature. In some embodiments, the controller may be arranged to control the pump may to dose a controlled volume of liquid substrate based on the first temperature and the second temperature. In some embodiments, the controller may be arranged to control the pump to dose a controlled volume of liquid substrate based on an air flow event, such as a volumetric air flow rate through the air flow passage. The pump may be arranged to dose a controlled volume of liquid substrate based on the amount of air flow passing through the air flow passage. In some embodiments, the liquid storage portion may be a removable cartridge. For example, the aerosol-generating device may comprise a connector, for connecting to a connector, such as a Luer fitting, of the cartridge.

In some embodiments, said first position is a position at the heating element and the first temperature is a temperature of the heating element at the first position, and said second position is a position downstream of the heating element and said second temperature is an ambient temperature of the airflow passage at said second position. In some embodiments, the device comprises a third temperature sensor for sensing a third temperature at a third position along the airflow passage, wherein said third position is a position upstream of the heating element and said third temperature is an ambient temperature of the airflow passage at said third position, and wherein the controller is configured to control the operational parameter of the device based on the first temperature, second temperature and third temperature. This may advantageously allow the controller to determine an air flow rate more accurately, by taking into consideration the heater temperature when comparing relative temperatures or temperatures changes that are measured upstream and downstream of the heating element.

In some embodiments, the temperature sensors may be on-chip temperature sensors. The temperature sensors may be planar. The temperature sensors may be embedded into a surface of the heating element. Thus the use of such on-chip temperature sensors may advantageously prevent excessive interruption to the air flowing in the air flow passage. In some embodiments, the surface of such on-chip temperature sensors may be coated with the nanoparticles for effecting surface plasmon resonance. Advantageously, the inclusion of such on-chip temperature sensors does not reduce a heating surface area available for effecting surface plasmon resonance.

The power supply is preferably, an electrical power supply, which may comprise a DC power supply. The electrical power supply may comprise at least one battery. The at least one battery may include a rechargeable lithium ion battery. The electrical power supply may comprise another form of charge storage device such as a capacitor. The electrical power supply may require recharging. The electrical power supply may have a capacity that allows for the storage of enough energy for one or more uses of the aerosol-generating device. For example, the electrical power supply may have sufficient capacity to allow for the continuous generation of aerosol for a period of around six minutes, corresponding to the typical time taken to smoke a conventional cigarette, or for a period that is a multiple of six minutes. In another example, the electrical power supply may have sufficient capacity to allow for a predetermined number of puffs or discrete activations.

In embodiments in which the aerosol-generating device comprises a plasmonic heating element and a light source, the controller may be configured to commence a supply of electrical power from the electrical power supply to the light source at the start of a heating cycle. The controller may be configured to terminate a supply of electrical power from the electrical power supply to the light source at the end of a heating cycle.

The controller may be configured to provide a continuous supply of electrical power from the electrical power supply to the light source.

The controller may be configured to provide an intermittent supply of electrical power from the electrical power supply to the light source. The controller may be configured to provide a pulsed supply of electrical power from the electrical power supply to the light source.

Advantageously, a pulsed supply of electrical power to the light source may facilitate control of the total output from the light source during a time period. Advantageously, controlling a total output from the light source during a time period may facilitate control of a temperature to which the plasmonic heating element is heated by surface plasmon resonance.

Advantageously, a pulsed supply of electrical power to the light source may increase thermal relaxation of free electrons excited by surface plasmon resonance compared to other relaxation processes, such as oxidative and reductive relaxation. Therefore, advantageously, a pulsed supply of electrical power to the light source may increase heating of the plasmonic heating element. Preferably, the controller is configured to provide a pulsed supply of electrical power from the electrical power supply to the light source so that the time between consecutive pulses of light from the light source is equal to or less than about 1 picosecond. In other words, the time between the end of each pulse of light from the light source and the start of the next pulse of light from the light source is equal to or less than about 1 picosecond.

The controller may be configured to vary the supply of electrical power from the electrical power supply to the light source. In embodiments in which the controller is configured to provide a pulsed supply of electrical power to the light source, the controller may be configured to vary a duty cycle of the pulsed supply of electrical power. The controller may be configured to vary at least one of a pulse width and a period of the duty cycle.

The aerosol-forming substrate may comprise a liquid aerosol-forming substrate. The aerosol-generating device may comprise a liquid transport element arranged to transport the liquid aerosol-forming substrate from the storage portion and towards the heating element. The liquid transport element may comprise a capillary wick.

The liquid aerosol-forming substrate may comprise water.

The liquid aerosol-forming substrate may comprise an aerosol-former. Suitable aerosol-formers are well known in the art and include, but are not limited to: polyhydric alcohols, such as triethylene glycol, 1,3-butanediol and glycerine; esters of polyhydric alcohols, such as glycerol mono-, di- or triacetate; and aliphatic esters of mono-, di- or polycarboxylic acids, such as dimethyl dodecanedioate and dimethyl tetradecanedioate. Preferred aerosol formers are polyhydric alcohols or mixtures thereof, such as triethylene glycol, 1,3-butanediol and, most preferred, glycerine or polyethylene glycol.

The liquid aerosol-forming substrate may comprise at least one of nicotine or a tobacco product. Additionally, or alternatively, the liquid aerosol-forming substrate may comprise another target compound for delivery to a user. In embodiments in which the liquid aerosol-forming substrate comprises nicotine, the nicotine may be included in the liquid aerosol-forming substrate with an aerosol-former.

The aerosol-generating device may comprise a first aerosol-forming substrate and a second aerosol-forming substrate. Preferably, the heating element is arranged to heat both the first aerosol-forming substrate and the second aerosol-forming substrate.

According to a third aspect of the present invention there is provided an aerosol-generating system comprising an aerosol-generating device according to the first and second aspects of the invention and an aerosol-generating article comprising an aerosol-forming substrate. The aerosol generating-article may comprise a liquid storage cartridge comprising the aerosol-forming substrate.

As used herein, an 'aerosol-generating device' relates to a device that may interact with an aerosol-forming substrate to generate an aerosol.

As used herein, the term 'aerosol-forming substrate' relates to a substrate capable of releasing volatile compounds that may form an aerosol. Such volatile compounds may be released by heating the aerosol-forming substrate.

The aerosol-forming substrate may be part of an aerosol-forming article. The aerosol-forming substrate may have any suitable configuration, and may include any of the features described in more detail below.

As used herein, the term 'aerosol generating system' refers to a combination of an aerosol-generating device and one or more aerosol-forming articles for use with the device. An aerosol-generating system may include additional components, such as a charging unit for recharging an on-board electric power supply in an electrically operated or electric aerosol-generating device.

According to a fifth aspect of the present invention, there is provided an aerosol-generating device comprising: an air inlet; an air outlet; an air flow passage extending in a first direction between the air inlet and the air outlet; a heating element in the air flow passage for heating an aerosol-forming substrate; a first temperature sensor for measuring a first temperature at a first position along the air flow passage; and a controller configured to control an operational parameter of the device based on at least the measured first temperature.

Features described in relation to one aspect may equally be applied to other aspects of the invention.

Figure 4:
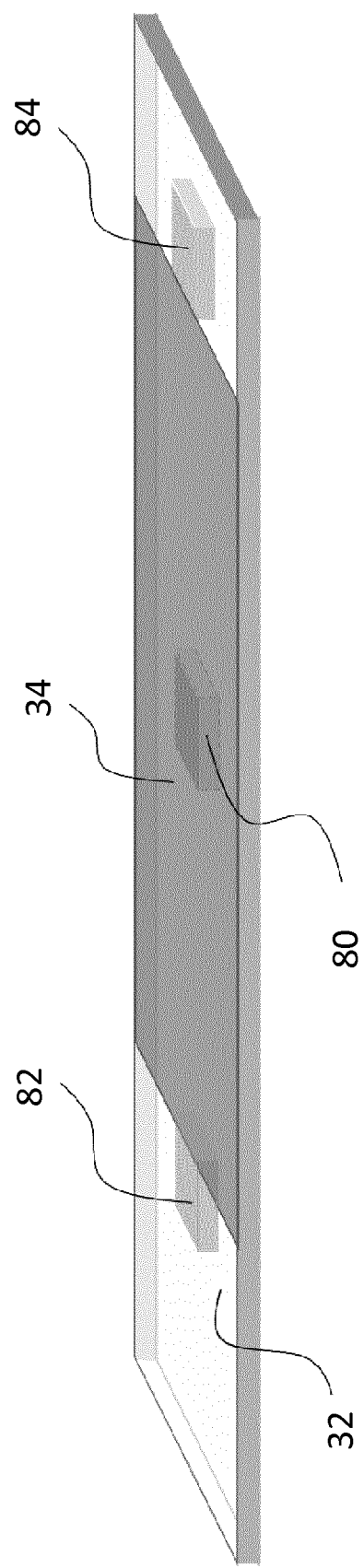
FIG. 4 is a perspective view of a heating element of an aerosol-generating device according to embodiments of the present invention.

Embodiments of the invention will now be described, by way of example only, with reference to the accompanying drawings, in which:

FIG. 1 is a perspective view of an aerosol-generating system according to an embodiment of the present invention;

FIG. 2*a* is an exploded perspective view of the heater assembly of FIG. 1;

FIG. 2*b* is a perspective view of the heater assembly of FIG. 1;

FIG. 2*c* is a sectional view of the heater assembly of FIGS. 2*a* and 2*b*;

FIG. 3 is a sectional view of the heater assembly according to an embodiment of the present invention;

FIG. 4 is an perspective view of a heating element of an aerosol-generating device according to embodiments of the present invention; and FIG. 5*a* is a schematic illustration of heat dissipation at the heating element of FIG. 4, in a first condition, in which there is substantially no air flow across the heating element; and FIG. 5*b* is a schematic illustration of heat dissipation at the heating element of FIG. 4, in a second condition, in which an air supply is drawn into the aerosol-generating device, across the heating element.

FIG. 1 shows an aerosol-generating system 10 comprising an aerosol-generating device 20 and a liquid storage portion 100 containing a liquid aerosol-forming substrate for use with the aerosol-generating device 20.

The aerosol-generating device 20 comprises a housing configured to receive the liquid storage portion 100, for example, in a storage compartment. The liquid storage portion 100 in the illustrated example of FIG. 1 is a replaceable cartridge comprising an aerosol-forming substrate, such as a liquid aerosol-forming substrate. The replaceable cartridge is connectable with a dosing unit 60 of the aerosol-generating device 20, by a leak proof connection 62, such as a Luer coupling, and tubing 64. The dosing unit 60, which in the illustrated examples comprises a pump, provides controlled delivery of liquid aerosol-forming substrate to a heater assembly 30, where the liquid substrate is heated to from a vapor. As a user puffs on a mouthpiece 66, an air supply is drawn into the aerosol-generating device 20 thought an air inlet 50. The air supply, at an ambient temperature, condenses the vapor to form a stream of generated aerosol. The mouthpiece 66 forms an air outlet 52. As a user puffs on the mouthpiece 66, the generated aerosol may exit the device into the user's mouth. Therefore, the air supply and generated aerosol flows in an air flow passage 43 defined between the air inlet 50 and air outlet 52.

The heater assembly 30 in the illustrated embodiment comprises a plasmonic heating element (e.g., heating element 32). The plasmonic heating element generates heat by surface plasmon resonance (SPR). Plasmonic heating elements generally comprise a plurality of metallic nanoparticles and are based on the excitation of the metallic nanoparticles with a light, for example visible light from a light source 40. The exposure to an incident light results in a collective oscillation of free electrons of the metallic nanoparticles and a polarization of charges at the surface of the metallic nanoparticles. In order to relax to their initial state, the nanoparticles release this surplus of energy in form of heat. Generally, the nanoparticles as used in plasmonic heaters have particle sizes that are equal to or less than the wavelength of the visible light.

The aerosol-generating device 20 comprises an electrical energy supply 12, for example a rechargeable lithium ion battery. The electrical energy supply 12 is comprises a charging port 16 for charging the rechargeable battery. The device 20 further comprises a controller 14 communicably coupled to one or more light sources. In the illustrated embodiment, the light sources comprise Light Emitting Diode (LED) 40. The controller is also communicably coupled to the electrical energy supply 12 and a user interface 26. In this embodiment, the user interface 26 comprises a mechanical button. Upon activating the user interface 26, the controller controls power supplied from the electrical energy supply 12 to the light source 40 in order to heat the heating element 32 to a required operating temperature. In some embodiments, the controller controls the power supplied to the light source 40 to provide a heating profile, such as a temperature profile, of the heating element over a period of time in which the device 20 is in use.

FIGS. 2a to 2c show an example of the heater assembly 30. In the illustrated embodiment, the heater assembly 30 comprises a heating element 32. A light source 40 is arranged in a position so as to emit light towards the heating element 32 when the light source 40 receives a supply of electrical power. The heater assembly 30 comprises an aerosol-generating chamber 38 between the light source 40 and the heating element 32. The aerosol-generating chamber 38 provides volume in which the liquid substrate may be vaporized to generate an aerosol with an incoming air supply. The aerosol-generating chamber 38 forms a part of an air flow passage 43 between the air inlet 50 and the air outlet 52. The air flow passage 43 extends along a first direction between the air inlet 50 and the air outlet 52. The first direction is coincident with or substantially parallel to a longitudinal axis of the device 20.

The heating element 32 in the illustrated embodiments comprises a planar element comprising a silicon based material, for example quartz, which is capable of maintaining its mechanical strength at an elevated temperature. The heating element 32 comprises a heating surface 34 extending across at least a part of the heating element 32 within the aerosol-generating chamber 38 for heating and vaporizing an incoming dose of liquid substrate. The heating surface 34 comprises the plurality of metallic nanoparticles for effecting surface plasmon resonance.

In this particular example, the heating surface 34 is coated with a layer of silver nanoparticles with a mean diameter of 100 nm, although nanoparticles of other sizes are also applicable. Alternatively other metal colloid or nanoparticles may be used, for example gold or platinum nanoparticles. A mixture of metallic nanoparticles may also be applied at the heating surface 34 for carrying out plasmonic heating, such as a mixture of gold and silver nanoparticles. As the quantity of nanoparticles is a critical factor governing a power output of the plasmonic heater, it is preferable to provide as many nanoparticles as possible on a given heating surface. Therefore, in order to increase the nanoparticle density and thus to increase heat generated by surface plasmon resonance, the heating surface, in some embodiments, comprises a plurality of nanoparticle layers for building up a total number of available metallic nanoparticles.

The light source 40 as illustrated comprises a Light Emitting Diode (LED). More specifically, the light source 40 comprises an array of LEDs each arranged to be independently controllable by the controller 14. For example, the plurality of LEDs may each emit light in a sequential manner, at different intensities, or at different wavelengths. This enables a variation in temperature rise across the heating surface. This is particularly beneficial because it also allows selective localised heating of the heating surface 34.

The light source 40 is arranged to align with the heating surface 34 of the heating element 32. For example, the light source 40 superimposes, but is spaced apart from the heating surface 34. This arrangement provides the metallic nanoparticles with maximum exposure to incident light emitted by the LED array. For example, the plurality of LEDs in the LED array may each emit light in a sequential manner, at different intensities, or at different wavelengths. This enables a variation in temperature across the heating surface. This is beneficial because it also allows selective localised heating. This may be used to correct for localized temperature fluctuations across the heating surface 34 of the heating element 32. In use, the light source 40 is arranged to cause the heating surface 34 to be heated to a temperature of between 200 and 350 degrees centigrade.

As illustrated in FIG. 2c, the device 20 comprises a lens 44 for refracting and focusing light emitted by the LED array towards the heating surface 34. The lens 44 is arranged between the LED light source 40 and the heating surface 34. For example, each of the LEDs in the LED array 40 comprises a lens formed integrally with the LED. An additional lens 44 is stack over the LED array. The refracted light may be focused or dispersed by the lens 44 to control how much light is transmitted to the heating surface 34 or portions thereof.

In some other embodiments, alternative light sources may be used as the light source. For example, the light source may comprise a laser diode. The laser diode permits maximum excitation of a particular type of nanoparticles. In some embodiments, the lens 44 of the heater assembly 30 may be in connection with a light conduit (not shown) extending towards an environment external to the housing of the device 20, to capture and transmit light from an external light source, such as natural daylight or ambient light, towards the heating surface 34 of the heating element 32. In such cases the external light collected at the lens 44 may be of a lower intensity in comparison to the artificial light source. Nevertheless, the external light source may be used for preheating the aerosol-forming substrate 102 to an elevated temperature above an ambient temperature, thus the power consumption at the artificial light source may accordingly be reduced.

The heater assembly 30 comprises a liquid channel 36 for feeding the liquid substrate to the heating surface 34. A single liquid channel 36 is shown in the figures, having an outlet adjacent to the heating surface 34. A plurality of liquid channels may also be provided. The use of plurality of liquid channels may advantageously diverge and feed the liquid substrate across a width of heating surface 34.

A capillary fitting 65 is provided for connecting the tubing 64 and the liquid channel 36. The capillary fitting 65 also forms a distributor for distributing a dose of liquid substrate evenly amongst the plurality of liquid channels 36.

The heater assembly 30 further comprises an air inlet 50 for drawing in an air supply. The air inlet 50 is in fluid communication with an air flow passage 43. As a user puffs on the mouthpiece 66, an air supply is drawn into the aerosol-generating chamber 38 from an environment external to the device 20 via the air inlet 50. When the heating element 32 is activated, air drawn in to the device is relatively cooler compared to ambient air within the device proximal to the heater. This relatively cooler air supply condenses at least a portion of vaporized aerosol-forming substrate in the aerosol-forming chamber 38, thereby forming a stream of generated aerosol.

The heat generated at the heating surface 34 by surface plasmon resonance radiates across the aerosol-generating chamber 38. This may heat up the LED light source 40. Advantageously, the flow of air supply through the aerosol generating chamber 38 via the air inlet 50 cools down the light source 40, thus protecting it from overheating.

In some embodiments, the heating surface 34 may comprise a plurality of discrete heating sections. This enables a temperature gradient across the heating surface 34 to more accurately be determined. In some embodiments, each heating section may comprise a different density of metallic nanoparticles or a different number of nanoparticle layers. This enables a variation in temperature rise across the different heating sections when all of the heating sections are exposed to a uniform light source. This is beneficial because it allows selective localised heating. For example, since upstream heating sections, proximal to the air inlet 50, may be more affected by relatively cooler incoming air, these heating sections may comprise relatively more nanoparticles in comparison to downstream heating sections proximal to the air outlet 52 and mouthpiece 66. In some cases, multiple heating sections also allows selective heating of aerosol-forming substrate, thus allowing different liquid substrates and flavoring compositions along the substrate to be heated to different temperatures.

The liquid storage portion 100 as used in the illustrated example is a replaceable cartridge. The replaceable cartridge 100 comprises flexible sidewalls and is arranged to collapse upon depletion of liquid aerosol-forming substrate. Depletion of liquid aerosol-forming substrate in the cartridge 100 does not cause a negative pressure in the liquid storage portion. Therefore the displacement of the liquid aerosol-forming substrate does not result in air bubbles being re-entering the cartridge 100. Thus reducing the likelihood of intermittent liquid substrate delivery caused by such air bubble and pump cavitation.

FIG. 3 shows a sectional view of another embodiment of the present invention. The aerosol-generating chamber 38b may comprise a tubular housing 22b. In this example, the aerosol-generating device 20b comprises the same components as the device 20 as shown in FIGS. 2a to 2c. The light source 40b and the lens 44b forms externally to the tubular housing 22b. The lens 44b is arranged to refract and focus the light 42 emitted by the light source 40b onto planar heating surface 34b at the heating element 32b. A portion of the tubular housing 22b comprises a support 24b for providing an even platform for supporting the heating element 32b, such as a planar heating element 32b.

FIG. 4 is a perspective view showing part of the heater assembly 30. The heater assembly 30 comprises the heating element 32 and a plurality of temperature sensors 80, 82, 84. In the illustrated embodiment, the plurality of temperature sensors comprise a heating element sensor 80 at the heating surface 34 for measuring the temperature at the heating element. The plurality of temperature sensors 80, 82, 84 further comprise an upstream sensor 82 and a downstream sensor 84 respectively located upstream and downstream of the heating surface 34. In this example, the upstream sensor 82 and the downstream sensor 84 are spaced apart, at equal distances from the heating surface 34, for measuring a temperature. The temperatures measured by the upstream sensor 82 and downstream sensor 84, may comprise an air temperature at or proximal to the position of the respective sensors 82, 84 or a temperature of a generated aerosol at or proximal to the position of the respective sensors 82, 84. As used herein, the phrase "upstream" refers to a position relatively closer to the air inlet 50 than to the air outlet 52. As used herein, the phrase "downstream" refers to a position relatively closer to the air outlet 52 than the air inlet 50.

The temperature sensors 80, 82, 84 may be on-chip temperature sensors. Such on-chip temperature sensors are generally planar and can be readily embedded in the heating element 32. Thus the use of these on-chip temperature sensors does not cause excessive interruption to the air flow pattern at the aerosol-generating chamber 38. In addition, the surface of such on-chip temperature sensors may be coated with metallic nanoparticles. This is particularly beneficial for the heating element sensor 80 because its inclusion does not reduce the amount of heating surface 34 available for effecting plasmonic heating.

The controller 14 is arranged to control an operational parameter of the device 20 based on at least two temperatures along the air flow passage 43. A temperature of the heating element 32 measured by the heating element sensor 80 may be sufficient for the controller 14 to provide feedback control over the power supply to the light source 40. More specifically, the controller 14 may be arranged to control an intensity, or a pulsing rate, or a combination of the intensity and the pulsing rate of the light as emitted by the light source 40, based on the measured heater temperature. This allows the temperature of the heating element 32 to be controlled to remain at a desired temperature or within a desired temperature range. The controller may apply conventional temperature control based on the measured heater temperature.

The use the plurality of temperature sensors 80, 82, 84 allows additional operational information, such as a temperature gradient across the heating surface 34, a temperature gradient across the aerosol-generating chamber 38 or an air flow event to be obtained. Based thereon, new control mechanisms may be applied. For example, the temperatures as measured at different locations across the aerosol-generating chamber 38 by the temperature sensors 80, 82, 84 may be used for determining an air flow event, such as an inhalation, an exhalation, or an air flow rate, such as a volumetric air flow rate, of the air supply. FIG. 5a shows an air temperature profile along the aerosol-generating chamber 38 when there is no air flow through the air flow passage 43. The heating surface 34 is energized by an incident light without the user puffing on the mouthpiece. For example, the user may engage with the user interface 26 to initiate a preheating of the heating element 32. A volume of stagnant air around the heating surface 34 is gradually heated by the heating surface 34, predominantly due to natural convection. As a result, the air temperature as shown in FIG. 5a progressively reduces with increasing distance from the heating surface 34. As shown in FIG. 5a, the temperature distribution of stagnant air around the activated heating element 32 us substantially symmetrical. Since the temperature is the same in both upstream and downstream direction, the upstream sensor 82 and the downstream sensor 84 detect similar air temperatures at each end of the heating surface 34. Such temperature reading indicates that there is no air flow in the chamber and thus the controller may cease power supply to the light source in order to prevent overheating at the heating surface 34, as well as conserving energy.

FIG. 5b shows another temperature profile along the aerosol-generating chamber 38 when a user puffs on the mouthpiece. In this example, there is an air supply 90 flowing in the direction from the upstream sensor 82 towards the downstream sensor 84. The ambient air supply displaces the stagnant air at the heater surface, thereby causing a reduction in air temperature as measured by the upstream sensor 82. On the other hand, the downstream sensor 84 would detect a rise in air temperature as the heated air and generated aerosol are carried towards the downstream sensor 84 by force convection. The relative changes in air temperatures as detected by the upstream sensor 82 and the downstream sensor 84 are related to a flow rate of the air supply 90. For example, a higher air flow increases the difference in temperatures as detected by the upstream sensor 82 and downstream sensor 84. As a result, the air flow rate of the air supply 90 may be determined from the two temperatures, such as from a difference or a ratio between the two temperatures measured by the sensors 82, 84 spaced apart from each other. This sensing may be used in combination with the heating element sensor 80, to provide a more accurate determination of a temperature gradient across the heating surface 34 of the heating element 32 in the aerosol-generating chamber 38.

The heater temperature, as measured by heating element sensor 80, in combination with only one of the upstream and downstream sensors 82, 84 may additionally be used in determining the air flow rate based on an enthalpy balance. A downstream temperature sensed by the downstream sensor 84 may be compared to the temperature of the heating element 32 so as to estimate a volume of air flowing between the heating element sensor 80 and the downstream temperature sensor 84. For example at a given temperature of the heating element, a relatively larger air flow rate would result in a relatively lower downstream temperature sensed by the downstream sensor 84 because the heating element provides heating to a larger volume of incoming air. The additional consideration of the temperature of the heating element 32 improves the accuracy of air flow rate calculation.

The controller 14 may refer to information stored in a memory in order to process one or more temperatures sensed by the sensors 80, 82, 84 or to determine how to control said operational parameter based on the one or more temperatures or both. The memory may be a non-transitory computer readable medium. The memory may be part of the aerosol-generating device, or may be remote to the device, such as a memory storage space on a cloud based server. The information may comprise at least one look up table. The information may comprise at least one algorithm. For example, a look-up table stored in the memory may provide an empirical air flow rate corresponding to different temperature measurements. The look-up table may also provide empirical air flow rate corresponding to different temperature measurements and a distance separating the temperature sensors.

The controller is arranged to control an operational parameter of the device 20 based directly on the measured temperature from the plurality of temperature sensors 80, 82, 84. The controller may be arranged to control an operational parameter of the device 20 based indirectly on the measured temperature from the plurality of temperature sensors 80, 82, 84. For example, the controller may be arranged to control an operational parameter of the device 20 based on an air flow event, such as an air flow rate determined from the measured temperatures, as above described. The operational parameter may comprise a plurality of operational parameters. The operational parameter may comprise one or more of any of: a temperature of the heating element 32, a temperature profile of the heating element 32, such as output temperature over time, power supplied directly or indirectly to the heating element 32, a flow rate of an aerosol-forming liquid substrate from the liquid storage portion 100 to the heating surface 34 and a dosage volume of the aerosol-forming liquid substrate supplied to the heating surface 34. As discussed above, the temperature or the temperature profile of the heating surface 34 may be controlled by the controller 14 controlling power supplied from the electrical energy supply 12 to the heating element 32 from a power supply to the heating element 32. The power may be supplied directly to the heating element 32. The power may be supplied indirectly to the heating element 32, for example by supplying electrical power the light source 40, which is arranged to provide light to a plasmonic heating surface 34 of the heating element 32.

In an exemplary embodiment, the aerosol-generating device 20 is arranged to control the flow rate of an aerosol-forming liquid substrate from the liquid storage portion 100 to the heating surface 34 in the following way. Firstly, the user activates the light source 40 by depressing the mechanical button of the user interface 26. Light is emitted from the light source 40 and falls incident on the metallic nanoparticles of the heating surface 34, to initiate surface plasmon resonance. As the nanoparticles on the heating surface 34 repeatedly undergo surface plasmon resonance followed by thermal relaxation, the temperature of the heating surface 34 increases to a desired operating temperature. Typically the heating surface 34 is heated to an operating temperature ranging from 200 to 350 degrees centigrade.

The controller 14 may determine when the temperature of the heating surface 34 of the heating element 32 reaches a first threshold temperature, such as the desired operating temperature. When the heating surface 34 reaches the first threshold temperature, the controller 14 activates the pump of the dosing unit 60 to feed the heating surface 34 with a dose of aerosol-forming liquid substrate once the desired operating temperature is reached. The controller 14 may cease or reduce the power supply to the light source when the heater temperature exceeds a second threshold temperature. The second threshold temperature may be relatively higher than the first threshold temperature and may relate to a predefined temperature limit. The controller 14 may therefore prevent overheating of the heating element.

The controller 14 may analyse a relationship, such as relative differences or ratios, between the temperature measurements obtained by the plurality of sensors 80, 82, 84. The controller 14 then determines, based on this analysis, an instantaneous air flow rate across the aerosol-forming chamber 38.

Based on the determined air flow rate, the controller 14 determines whether an adjustment of the temperature of the heating surface 34 is required. For example, as a user puffs on the mouthpiece 66, ambient air is drawn through the air inlet 50, into the aerosol-generating chamber 38. This incoming air initially has a cooling effect on at least a part of the heating surface 34 of the heating element 32. Therefore, upon detection of an inhalation, the controller 14 may determine that a temperature adjustment, such as an increase in temperature at the heating surface 34, is required. When the controller determines that a temperature adjustment is required, the controller 14 determines a required amount of power to be supplied to the light source 40 to effect the determined temperature adjustment. The controller 14 may therefore control the temperature of the heating surface 34 to correct for cooling induced by an incoming air supply as the user puffs on the mouthpiece 66. This helps to maintain a consistent operating temperature at the heating surface 34 of the heating element 32, whilst the user operates the device. Overheating of the heating element 32 may therefore be prevented. Overcooling at the heating surface 34 due to fluctuations in the incoming air may also be prevented.

In some embodiments, based on the determined air flow rate, the controller may also determine the amount of aerosol-forming liquid substrate required to be dosed at the heating surface 34. The controller 14 subsequently adjusts operation of the pump of the dosing unit 60 to control the rate of aerosol-forming liquid substrate delivery to the heating surface 34. More specifically, the amount of liquid substrate as dosed onto the heating surface 34 can be made proportional to the air flow rate. This may allow for a consistent aerosol concentration in each puff, regardless of how hard the user draws on the mouthpiece 66.

In some embodiments, the pump of the dosing unit 60 is arranged to deliver a fixed quantity of liquid substrate upon detecting an air flow, such as an air flow indicative of the user puffing on the mouthpiece 66 of the device 20. For example, upon detecting a temperature difference between the upstream sensor 82 and the downstream sensor 84, the controller 14 outputs a signal to the dosing unit 60 to deliver a fixed dose of aerosol-forming liquid substrate onto the heating surface 34. In comparison to a continuous pumping system where aerosol-forming liquid substrate is continuously delivered upon heater activation, this arrangement limits an amount of aerosol generated per puff. Where the aerosol-forming liquid substrate comprises nicotine, nicotine in the aerosol, delivered in each puff, is therefore limited. This may provide a consistent delivery of nicotine throughout a session of use of the device.

In some embodiments, the controller 14 is arranged to supply power to the light source 40 only when an air flow is detected passing through the aerosol-generating chamber 38. In such embodiments, the heating surface 34 may only be heated when generated aerosol is withdrawn through the aerosol-generating chamber 38. This prevents liquid substrate from drying out at the heating surface 34, as well as safeguarding the heater assembly 30 from overheating.

In some embodiments, the controller 14 is arranged to monitor the user's puffing behavior based on the determined air flow rate. The controller 14 may determine a puff rate, a puff frequency, a puff volume, or any combination thereof. The controller 14 may then determine the total amount of aerosol-forming liquid substrate being inhaled by the user over each usage cycle. Where the aerosol-forming liquid substrate comprises nicotine, the controller 14 may determine the total amount of nicotine being inhaled by the user over each usage cycle. This allows safety limits to be implemented to limit an amount of nicotine inhalable by a user over a given time period. For example, the aerosol-generating device 20 may reduce the dosage of aerosol-forming liquid substrate, or may cease operating, when the user approaches or exceeds a predefined nicotine limit in each usage cycle.

In some embodiments, the controller 14 may reference the monitored puffing behavior and modify a feedback control provided to the pump of the dosing unit 60 and the heater assembly 30. For example, the controller 14 may determine an average puff duration or an average pause duration between puffs for a particular user. The controller 14 may subsequently apply this information for controlling the heating and dosing of aerosol-forming liquid substrate. The controller 14 may automatically pause the heating and dosing of liquid substrate upon the lapse of an average puff duration. The controller 14 may also resume heating the heating surface 34 when the average pause duration is about to expire. This allows prompt aerosol generation and delivery, whilst improving efficiency of the device 20.

In some embodiments, the aerosol-generating device 20 only comprises two or fewer of the plurality of temperatures sensors 80, 82, 84. This arrangement reduces the amount of data that needs to be analyzed, thus reducing the complexity in process control. For example, the determination of an air flow rate across the aerosol-generating chamber 38 may be achieved using only two temperature sensors spacing apart from each other. More specifically in one embodiment, only the upstream sensor 82 and the downstream sensor 84 are provided without the heating element sensor 80. The control of heater temperature and dosing of liquid substrate may therefore be based on the temperature across the two sensors 82, 84, as well as a determined air flow rate as discussed in the earlier embodiment relating to FIG. 5b.

In some embodiments, only the heating element sensor 80 and the downstream sensor 84 are provided in the aerosol-generating device 20. The air flow rate through the aerosol-generating chamber 38 may be determined based on the difference in the heater temperature and the air temperature downstream to the heating surface 34. More specifically, the air flow rate may be determined by determining an amount of heat dissipation at a particular temperature of the heating surface 34 of the heating element 32. The controller 14 may refer to a look-up table as stored at a memory, so as to improve the accuracy in determining air flow rate. The look-up table provides empirical air flow rate corresponding to different downstream temperatures and heater temperatures. The look-up table may also provide empirical air flow rate corresponding to different downstream temperatures, different heater temperatures and a distance separating downstream sensor 84 to the heating surface 34.

In some embodiments, only one upstream sensor 82 is provided in the vicinity of the heating surface 34. For example, the temperature reading at the upstream sensor 82 may allow the controller 14 to determine a frequency and duration of each puff, based on an amount of cooling upstream of the heating surface 34 induced by the incoming air supply. When there is no air flow in the air flow channel, as shown in FIG. 5a, the upstream air temperature warms up gradually whilst the heating surface 34 is activated. As a user puffs on the mouth piece 66, the incoming air supply causes a dip in a measured upstream temperature. Therefore a time history, or a change in temperature over time, of upstream temperature is indicative of a flow of air supply and thus the user's puff behavior. The use of upstream sensor 82 may also serve as an automatic trigger for heating the heating surface 34 and pumping of liquid substrate.

In some embodiments, only the downstream sensor 84 is provided in the aerosol-generating device 20. More specifically, the heating element sensor 80 and the upstream sensor 82 are omitted. By referring to a look-up table, the controller 14 is arranged to estimate the heater temperature from the power consumed by the light source 40. The controller may subsequently determine the air flow rate based on the difference in the estimated heater temperature and the air temperature measured by the downstream sensor 84, using the method as described in relation to the embodiment as shown in FIG. 5b.

In some embodiments, a plurality of heating element sensors 80 are provided along the length of heating surface 34. The heating surface 34 comprises a plurality of heating sections. Each of the heating element sensors 80 are provided in a respective heating section for detecting a localized heating section temperature. Each of the heating sections is independently energizable by a respective local light source. For example, each of the local light sources is an LED in the LED array 40.

In use, a lack of air flow across the aerosol-generating chamber 38 results in a lack of air cooling at the heating surface 34, thus heating section temperatures as measured by each of the heating element sensors 80 should return a similar value. As the user puffs on the mouthpiece 66, the incoming air supply cools down the portion of heating surface 34 that is closest to the air inlet, such as an upstream heating surface. This results in different temperature readings over the plurality of heating element sensors 80 across the different heating sections. Thus, an air flow rate can be determined based on the relative difference between the heater temperatures as measured across the different heating sections.

Furthermore, the plurality of heating element sensors 80 as installed along the heating surface 34 permits localize heating control. For example, the controller is arranged to control the power as supplied to each of the local light sources based on the respective heating element sensor 80. This is particularly beneficial as more power can be supplied to the local light source for energizing the upstream heating section, in order to compensate for the cooling induced by the ambient air supply.

The exemplary embodiments described above illustrate but are not limiting. In view of the above discussed exemplary embodiments, other embodiments consistent with the above exemplary embodiments will now be apparent to one of ordinary skill in the art.

The invention claimed is:

1. An aerosol-generating device, comprising:
    an air inlet;
    an air outlet;
    an air flow passage extending in a first direction between the air inlet and the air outlet;
    a heating element in the air flow passage;
    a first temperature sensor configured to measure a first temperature at a first position along the air flow passage, wherein the first position is a position at the heating element and the first temperature is a temperature of the heating element at the first position;
    a second temperature sensor spaced apart in the first direction from the first sensor configured to measure a second temperature at a second position along the air flow passage, wherein the second position is a position downstream of the heating element and the second temperature is an ambient temperature of the air flow passage at the second position;
    a third temperature sensor configured to measure a third temperature at a third position along the air flow passage, wherein the third position is a position upstream of the heating element and the third temperature is an ambient temperature of the air flow passage at the third position; and
    a controller configured to control an operational parameter of the aerosol-generating device based on the measured first temperature, the measured second temperature, and the measured third temperature.

2. The aerosol-generating device according to claim 1,
    wherein the heating element comprises a plurality of heating sections, and
    wherein each of the first temperature sensor and the second temperature sensor is positioned at a respective heating section of the heating element.

3. The aerosol-generating device according to claim 2, wherein the controller is further configured to determine a temperature distribution across the plurality of heating sections, and to control power supplied to the plurality of heating sections based on the determined temperature distribution.

4. The aerosol-generating device according to claim 1, wherein the controller is further configured to determine a temperature distribution across the heating element, and to control the operational parameter based on the determined temperature distribution.

5. The aerosol-generating device according to claim 1,
    wherein the operational parameter of the device comprises a temperature of the heating element, and
    wherein the controller is further configured to control an output temperature of at least a portion of the heating element based on the measured first temperature and the measured second temperature.

6. The aerosol-generating device according to claim 1, wherein the controller is further configured to determine an air flow rate through the air flow passage based on the measured first temperature and the measured second temperature.

7. The aerosol-generating device according to claim 6, wherein the controller is further configured to control the operational parameter based on the determined air flow rate.

8. An aerosol-generating system comprising the aerosol-generating device according to claim 1; and an aerosol-generating article comprising an aerosol-forming substrate.

9. An aerosol-generating device, comprising:
    an air inlet;
    an air outlet;
    an air flow passage extending in a first direction between the air inlet and the air outlet;
    a heating element in the air flow passage configured to heat an aerosol-forming substrate;
    a first temperature sensor configured to measure a first temperature at a first position along the air flow passage;
    a second temperature sensor spaced apart in the first direction from the first sensor configured to measure a second temperature at a second position along the air flow passage;
    a controller configured to control an operational parameter of the device based on the measured first temperature and the measured second temperature;
    a liquid storage portion comprising the aerosol-forming substrate; and
    a pump configured to pump the aerosol-forming substrate from the liquid storage portion to the heating element,
    wherein the operational parameter of the aerosol-generating device comprises a flow rate of the aerosol-forming substrate from the liquid storage portion to the heating element, and
    wherein the controller is further configured to control the flow rate of the aerosol-forming substrate based on the measured first temperature and the measured second temperature.

10. The aerosol-generating device according to claim 9,
    wherein the heating element comprises a plurality of heating sections, and
    wherein each of the first temperature sensor and the second temperature sensor is positioned at a respective heating section of the heating element.

11. The aerosol-generating device according to claim 10, wherein the controller is further configured to determine a temperature distribution across the plurality of heating sections, and to control power supplied to the plurality of heating sections based on the determined temperature distribution.

12. The aerosol-generating device according to claim 9, wherein the controller is further configured to determine a temperature distribution across the heating element, and to control the operational parameter based on the determined temperature distribution.

13. The aerosol-generating device according to claim 9, wherein the operational parameter of the device comprises a temperature of the heating element, and
wherein the controller is further configured to control an output temperature of at least a portion of the heating element based on the measured first temperature and the measured second temperature.

14. The aerosol-generating device according to claim 9, wherein the controller is further configured to determine an air flow rate through the air flow passage based on the measured first temperature and the measured second temperature.

15. The aerosol-generating device according to claim 14, wherein the controller is further configured to control the operational parameter based on the determined air flow rate.

16. A method of controlling an aerosol-generating device, the aerosol-generating device comprising a heating element in an air flow passage extending in a first direction, the method comprising:
   measuring a first temperature at a first position along the air flow passage, wherein the first position is a position at the heating element and the first temperature is a temperature of the heating element at the first position;
   measuring a second temperature at a second position along the air flow passage, wherein the second position is spaced apart in the first direction from the first position, wherein the second position is a position downstream of the heating element, and the second temperature is an ambient temperature of the air flow passage at the second position;
   measuring a third temperature at a third position along the air flow passage, wherein the third position is a position upstream of the heating element and the third temperature is an ambient temperature of the air flow passage at the third position; and
   controlling an operational parameter of the device, based on the measured first temperature, the measured second temperature, and the measured third temperature, the operational parameter being a parameter that affects operation of one or more components of the aerosol-generating device.

17. A method of controlling an aerosol-generating device, the aerosol-generating device comprising a heating element in an air flow passage extending in a first direction, a liquid storage portion comprising an aerosol-forming substrate, and a pump configured to pump the aerosol-forming substrate from the liquid storage portion to the heating element, the method comprising:
   measuring a first temperature at a first position along the air flow passage;
   measuring a second temperature at a second position along the air flow passage, wherein the second position is spaced apart in the first direction from the first position; and
   controlling an operational parameter of the device, based on the measured first temperature and the measured second temperature, wherein the operational parameter of the device comprises a flow rate of the aerosol-forming substrate from the liquid storage portion to the heating element, and wherein the controlling the operational parameter of the device comprises controlling the flow rate of aerosol-forming substrate based on the measured first temperature and the measured second temperature.

* * * * *